United States Patent
Kobayashi et al.

(10) Patent No.: US 7,992,994 B2
(45) Date of Patent: Aug. 9, 2011

(54) PROCESS OF PRODUCING BREATHABLE SHEET AND PROCESS OF PRODUCING ABSORBENT ARTICLE

(75) Inventors: Hideyuki Kobayashi, Tochigi (JP); Akihiko Gunji, Tochigi (JP)

(73) Assignee: Kao Corporation, Tokyo (JP)

( * ) Notice: Subject to any disclaimer, the term of this patent is extended or adjusted under 35 U.S.C. 154(b) by 1404 days.

(21) Appl. No.: 11/229,613

(22) Filed: Sep. 20, 2005

(65) Prior Publication Data
US 2006/0070701 A1 Apr. 6, 2006

(30) Foreign Application Priority Data
Oct. 1, 2004 (JP) .................................. 2004-290697

(51) Int. Cl.
*B41J 2/01* (2006.01)
(52) U.S. Cl. ......... 347/107; 347/105; 347/106; 347/101
(58) Field of Classification Search .................. 347/101, 347/103, 105–107, 102; 428/195, 32.1, 32.16
See application file for complete search history.

(56) References Cited

U.S. PATENT DOCUMENTS

| | | | | |
|---|---|---|---|---|
| 5,458,590 A * | 10/1995 | Schleinz et al. | ............. | 604/361 |
| 5,650,808 A * | 7/1997 | Vincent et al. | ................ | 347/43 |
| 6,432,514 B1 * | 8/2002 | Kobayashi et al. | ......... | 428/32.16 |
| 6,824,839 B1 * | 11/2004 | Popat et al. | ................ | 428/32.12 |
| 7,303,651 B2 * | 12/2007 | Asano et al. | ................ | 162/135 |
| 2002/0028319 A1 * | 3/2002 | Hirabayashi et al. | ......... | 428/195 |
| 2003/0048343 A1 * | 3/2003 | Anderson et al. | ............. | 347/101 |
| 2003/0231234 A1 * | 12/2003 | Ushirogouchi et al. | ...... | 347/100 |
| 2004/0066441 A1 * | 4/2004 | Jones et al. | ................ | 347/101 |
| 2004/0119804 A1 * | 6/2004 | Emslander et al. | ........... | 347/105 |
| 2004/0125184 A1 | 7/2004 | Sharma et al. | | |
| 2005/0078162 A1 * | 4/2005 | Shinohara et al. | ............ | 347/105 |
| 2005/0128277 A1 * | 6/2005 | Quintana et al. | ............. | 347/105 |
| 2006/0004333 A1 * | 1/2006 | Olson | ............ | 604/361 |
| 2007/0043331 A1 * | 2/2007 | Haruki et al. | ............. | 604/385.3 |

FOREIGN PATENT DOCUMENTS

| | | |
|---|---|---|
| EP | 0777008 A1 | 6/1997 |
| GB | 2177977 A | 2/1987 |
| JP | 62-69802 A | 3/1987 |
| JP | 2000-266 A | 1/2000 |
| JP | 2001-518984 A | 10/2001 |
| WO | WO-98/43821 A1 | 10/1998 |

OTHER PUBLICATIONS

Japanese Notice of Rejection dated Feb. 3, 2009 issued in JP2004-290697 (with partial English translation).

* cited by examiner

*Primary Examiner* — Matthew Luu
*Assistant Examiner* — Henok Legesse
(74) *Attorney, Agent, or Firm* — Birch, Stewart, Kolasch & Birch, LLP

(57) ABSTRACT

A hot melt adhesive is applied to a side of a fibrous sheet 1 (e.g., nonwoven fabric) with an applicator 2 to form an adhesive layer 3. Ink drops are ejected from an inkjet head 5 onto either (1) the adhesive layer 3 on that side of the fibrous sheet or (2) the opposite side of the fibrous sheet within the area corresponding to the adhesive layer 3.

3 Claims, 5 Drawing Sheets

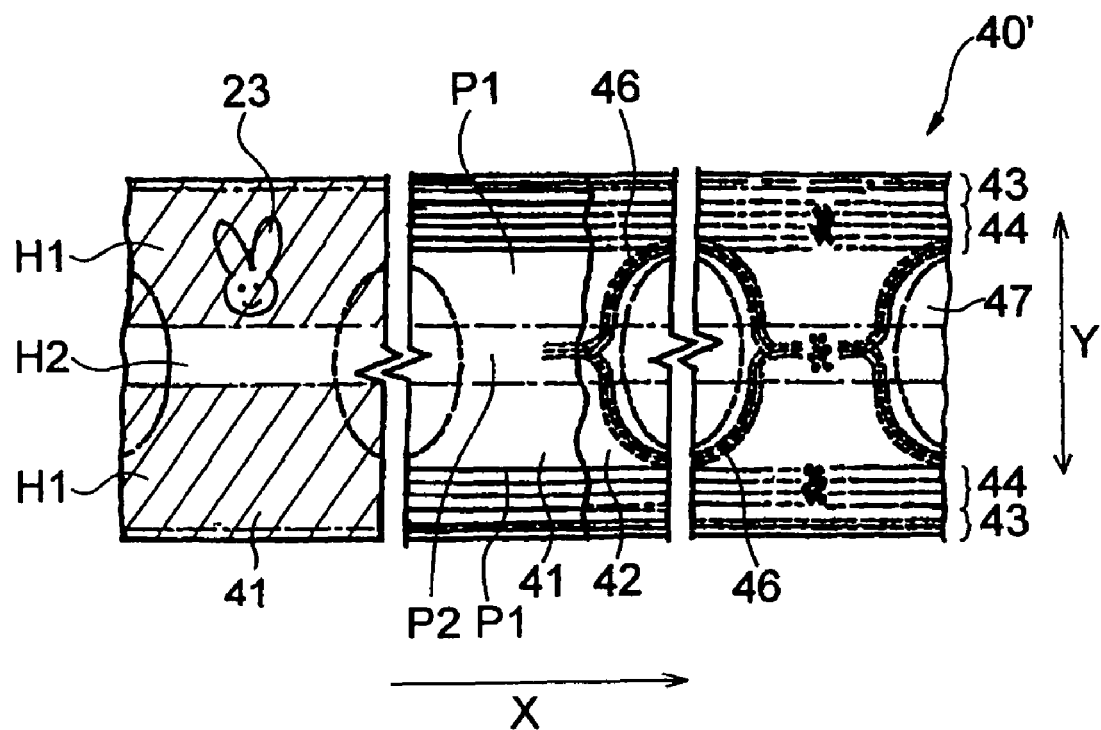

PROCESS OF PRODUCING BREATHABLE SHEET AND PROCESS OF PRODUCING ABSORBENT ARTICLE

TECHNICAL FIELD

The present invention relates to a process of producing a breathable sheet with a printed pattern and a process of producing an absorbent article having the breathable sheet.

BACKGROUND ART

Sheeted materials containing fibers in a large proportion, such as nonwoven fabric, synthetic paper, and woven fabric (hereinafter referred to as a fibrous sheet) are used as material of a disparate range of products including articles requiring breathability. In the manufacture of articles printed with a decorative pattern, a brand mark of the manufacturer, etc, these fibrous sheets are not infrequently used as a printing medium. For example, in the field of absorbent articles such as disposable diapers and sanitary napkins, nonwoven fabrics are applied as various members exemplified by an exterior sheet (backsheet) disposed on the garment-facing side of an absorbent material. In these kinds of absorbent articles, printing a pattern has been often done on their plastic film such as a backsheet but recently sometimes done on a nonwoven fabric of its external laminate or a nonwoven fabric for a commercial package. Gravure printing or flexographic printing has been used to print nonwoven fabrics but recently replaced with inkjet printing as described, e.g., in JP-A-62-69802 and JP-A-2000-266. Inkjet printing is a printing technique where drops of ink ejected from minute inkjet head nozzles are applied to a substrate to be printed. Inkjet printing requires no printing plate and achieves high-speed printing with relatively simple equipment. Incorporated into the production process of an absorbent article, inkjet printing allows for efficient production of absorbent articles with a wide variety of printed patterns as designed.

Fibrous sheets fit for inkjet printing have been proposed. Among them is a laminate composed of a cellulosic nonwoven web and nonwoven fabric containing a natural or synthetic polymer joined via an adhesive, which is proposed in JP-A-2001-518984 as an inkjet printable material providing a printed sheet material free from feathering and excellent in colorfastness to washing.

DISCLOSURE OF THE INVENTION

When inkjet printed, a fibrous sheet such as nonwoven fabric sometimes suffers from strike-through, a fault caused by ink penetrating through the fibrous sheet. If this happens, guide rolls of equipment will be soiled with the ink, which is transferred to the product to spoil the product. In recent years, nonwoven fabrics have been reducing in thickness, and the tendency to strike-through is increasing accordingly. In high-speed inkjet printing, in particular, because the ink drops are small to achieve high resolution, and the ink drop ejection speed is high, the ink droplets easily penetrate through a fibrous sheet to cause strike-through. Accordingly, strike-through is a problem waiting for a prompt solution in order to realize a further increased printing speed. Furthermore, if strike-through occurs, that means part of ink that should have been used to print a pattern makes no contribution to pattern formation, which can result in insufficient printing density, failing to obtain a clear printed pattern. In addition, an ink pattern inkjet-printed on a fibrous sheet has insufficient fastness (fixability) and can come off by slight rubbing or wetting with water.

It is an object of the present invention to provide a process of producing a breathable sheet, which is inkjet printable without strike-through to have a printed pattern with excellent fastness and a process of producing an absorbent article containing the breathable sheet.

To accomplish the above object, the present invention provides a process of producing a breathable sheet having a pattern printed thereon. The process includes the steps of applying a hot melt adhesive to one side of a fibrous sheet and inkjet printing the pattern on the side of the fibrous sheet in the area having the hot melt adhesive applied or the other side of the fibrous sheet in the area corresponding to the area having the hot melt adhesive applied.

To accomplish the above object, the present invention also provides a process of producing an absorbent article having an absorbent body and an exterior laminate on the garment facing side of the absorbent body. The process includes the steps of applying a hot melt adhesive to one side of a fibrous sheet, inkjet printing the pattern on the side of the fibrous sheet in the area having the hot melt adhesive applied or the other side of the fibrous sheet in the area corresponding to the area having the hot melt adhesive applied, and disposing the printed fibrous sheet as a member of the exterior laminate with the printed side not being exposed outward.

BRIEF DESCRIPTION OF THE DRAWINGS

FIG. 5(a), FIG. 5(b), and FIG. 5(c) each schematically illustrate a step involved in an embodiment of production of the exterior laminate used in the absorbent member of FIG. 3.

DETAILED DESCRIPTION OF THE INVENTION

The process of producing a breathable sheet according to the present invention will be described with reference to its preferred embodiment by way of the accompanying drawings.

Figure 1:
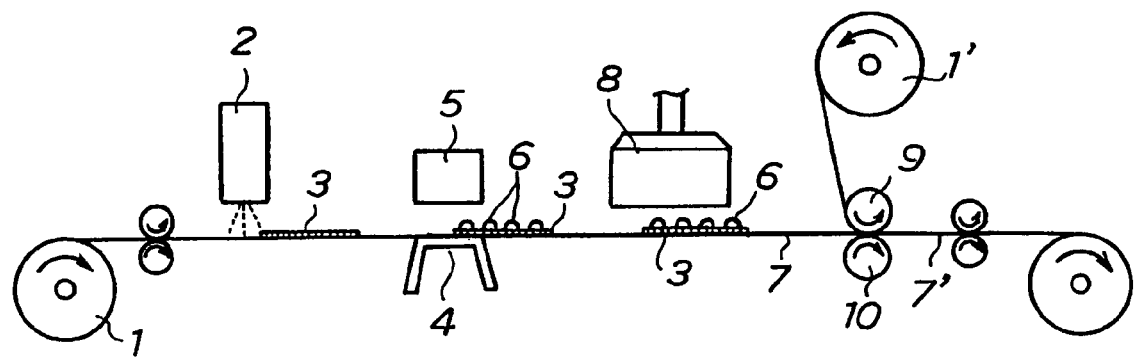
FIG. 1 schematically illustrates an embodiment of the process for producing a breathable sheet according to the present invention.

The breathable sheet, an object of the production process of the present invention, is a fibrous sheet having a pattern printed thereon. FIG. 1 is a schematic illustration of an embodiment of the production process of the present invention. In the embodiment, a fibrous sheet 1 is unrolled, and a hot melt adhesive is applied to one side of the fibrous sheet 1 to form an adhesive layer (coated area) 3 on that side. The hot melt adhesive application is carried out with an adhesive applicator 2.

The fibrous sheet includes those containing natural fiber (e.g., cellulose) and/or synthetic fiber made from thermoplastic resins (e.g., polyethylene, polypropylene and polyester) as a major component, namely, a sheet containing 50% by weight or more of fiber on a dry basis. Not only sheets made of absorbent fiber but also those made of non-absorbent fiber are usable. The fibrous sheet can contain ground pulp or an inorganic or organic pigment. Fibrous sheets suitably used in the present invention include nonwoven fabrics. Synthetic paper and woven fabrics also serve as a fibrous sheet to be printed. Although carded nonwoven fabrics usually contain textile oil and tend to have poor ink fixability, the process of the present invention achieves printing with high fastness even on carded nonwoven fabrics. Moreover, the present invention makes it possible to print a lightweight, thin fibrous sheet without causing strike-through. Thus, the process is applicable to a fibrous sheet as light as 30 g/m$^2$ or less. Particularly preferred is a fibrous sheet weighting 22 g/m$^2$ or less, more preferably 16 g/m$^2$ or less, for its breathability and flexibility. From the standpoint of strength the fibrous sheet should have a weight of 4 g/m$^2$ at the lightest.

Examples of hot melt adhesives that can preferably be used in the present invention include styrene elastomers, such as SIS (styrene-isoprene-styrene block copolymer), SBS (styrene-butadiene-styrene block copolymer), SIBS (styrene-isoprene-butadiene-styrene block copolymer), SEBS (styrene-ethylene-butylene-styrene block copolymer), and SEPS (styrene-ethylene-propylene-styrene block copolymer); an ethylene-vinyl acetate copolymers; polyester, acrylic or polyolefinic elastomers; and rubbers, such as polyisobutylene, butyl rubber, polyisoprene, and natural rubber. More preferred of them are styrene elastomers; for they are easily formed into a fiber and uniformly applicable. The hot melt adhesive application system is not limited, and known systems can be utilized, including a coater system, a spiral system (omega pattern or dura weave pattern), a spray system, and a curtain spray system.

The adhesive layer 3 (hot melt adhesive coated area) is preferably applied in a fiber form to make a net pattern composed of a great number of hot melt adhesive fibers randomly joined to each other. The adhesive layer 3 applied in a net pattern (an aggregate of hot melt adhesive fibers, hereinafter referred to as an adhesive fiber net) averts reduction of breathability due to adhesive application. In order for the adhesive fiber net to withstand the impact by inkjet droplets and to have a mesh with some fineness, the diameter of the hot melt adhesive fiber is preferably 0.5 to 30 μm. In order to trap ink droplets without fail, the average interfiber distance of the adhesive fiber net is preferably 5 μm or less. The interfiber distance can be obtained by dividing the length of a fiber by the number of fibers intersecting with that fiber and subtracting the fiber diameter from the quotient on an electron micrograph.

The adhesive fiber net can successfully be formed by a curtain spray application system. An ordinary adhesive applicator using a curtain spray system, namely a curtain spray coater, has small orifices aligned linearly and air ejecting nozzles near each orifice. Hot air ejected from the nozzles at a high speed is applied to a molten, filamentous, hot melt adhesive extruded from the orifices to draw and shred the filamentous adhesive into discrete fine fibers. In this way, the hot melt adhesive extruded from a large number of orifices is converted into short fine fibers and fall on the running fibrous sheet 1. The result is a net made of a large number of fibers randomly intersecting with each other, i.e., the adhesive layer 3, on the fibrous sheet 1.

Another preferred form of the adhesive layer 3 (hot melt adhesive coated area) is a porous film, i.e., a continuous hot melt adhesive film having fine through-holes. Such an adhesive porous film can be formed by applying a hot melt adhesive by a contact coater system. The adhesive porous film secures breathability by its perforations and exhibits high ink fixability by its non-perforated part to trap ink droplets.

The coating weight of the hot melt adhesive is preferably at least 0.5 g/m$^2$ on a solid basis, taking into consideration effective prevention of strike-through in inkjet printing, satisfactory ink fixability, uniformity of the adhesive layer applied, and sufficient adhesive strength to another sheet. Considering that too much adhesive application results in serious reduction in breathability, the coating weight is more preferably 0.8 to 7 g/m$^2$, even more preferably 1.5 to 5 g/m$^2$. Within that range, sufficient flexibility of the sheet can be secured. It is preferred for the finally obtained breathable sheet to have an air permeability of 0.002 sec/ml or more as measured with a Frazier or Gurley air permeability instrument as specified in JIS L1096. A more preferred air permeability is 0.005 to 0.07 sec/ml for satisfying both strike-through prevention and high breathability.

A desired pattern is then printed on the adhesive layer 3 (hot melt adhesive coated area) by inkjet printing. An ink jet head 5 serially scans the adhesive layer 3 on a printing mount 4 in the fast scanning direction, the direction perpendicular to the running direction (slow scanning direction) of the fibrous sheet 1, to eject color inks from the respective nozzles in accordance with the printing image data from a host computer (not shown), thereby to adhere ink 6 by prescribed pattern to the adhesive layer 3. What is actually adhered to the adhesive layer 3 is the solids content of the ink, such as a colorant. Since inkjet printing is a contactless printing system using very fine ink droplets, even when printing image data is a 100% duty cycle (so-called solid printing), the ink (colorant), in fact, does not completely cover the surface to be printed so that the adhesiveness of the adhesive layer 3 will not be completely impaired by the inkjet printing. Therefore, it is still possible for the printed adhesive layer 3 alone to bond the breathable sheet with another sheet (described later).

Mechanisms of ink drop formation in inkjet printing include an electro-thermal system using an electro-thermal element (e.g., a heater) typified by Bubble Jet™ system proposed by Canon, an electromechanical system using a piezo-electric element, and a system utilizing a static electricity generating means such as electrodes, any of which can be used in the present invention. Any kinds of ink are useful as long as they are fit for inkjet printing. Ink commonly used in inkjet printing is a solution or dispersion of a dye or a pigment in water or an alcohol, which can contain a wetting agent, a penetrant, etc. according to necessity. In full color printing, inks of at least three subtractive primaries, yellow, magenta and cyan (and often black) are used.

The result of inkjet printing a desired pattern on the adhesive layer 3 (the hot melt adhesive coated area) is a breathable sheet 7 as an object of the production process of the present invention.

The inkjet printing is desirably carried out immediately after hot melt adhesive application in order to accelerate ink drying. Specifically, it is preferred to conduct inkjet printing while the adhesive layer 3 (the applied hot melt adhesive) is at 40° C. or higher, more preferably 60° C. or higher. By applying ink to the adhesive layer 3 while the adhesive layer 3 keeps some heat, the ink drying time can be reduced. Reduction in ink drying time is not only expected to bring about improved production efficiency but effective in avoiding ink smudging or feathering that might occur when ink dries slowly. There is another advantage that an equipment or step for ink drying can be simplified or even omitted.

A higher inkjet printing speed (i.e., a higher running speed of the fibrous sheet) would be preferred from the standpoint of breathable sheet production efficiency. Nevertheless an increased printing speed must be accompanied by an increased resolution and an increased ink drop ejection speed so as to prevent the printed image from becoming unclear. That tends to result in an increased number of ink drops that strike through the fibrous sheet, i.e., an increased strike-through incidence rate. In high-speed inkjet printing at a printing speed of 100 m/min or higher, the resolution and the ejection speed are usually 150 dpi or more and 8000 dot/sec or more, respectively. Under such conditions a fibrous sheet is very liable to ink strike-through. According to the present invention, in contrast, ink strike-through can effectively be prevented from occurring even under such severe inkjet printing conditions by the action of the hot melt adhesive. In other words, the present invention can be said to be especially effective in high-speed inkjet printing at a printing speed of 100 m/min or higher.

Figure 2A:
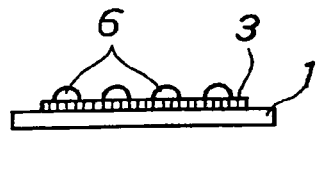
FIG. 2(a) and FIG. 2(b) each schematically represent a cross-section of a breathable sheet according to the present invention.
Figure 2B:
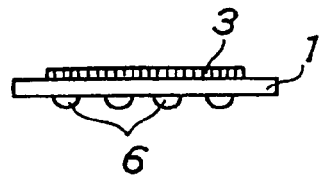

In the present embodiment illustrated in FIG. 1, a pattern is printed by applying ink 6 directly onto the area coated with the hot melt adhesive (the adhesive layer 3) on one side of the fibrous sheet 1 as shown in FIG. 2(a). Alternatively, the ink 6 may be applied to the other side of the fibrous sheet 1 within the area corresponding to the adhesive-coated area of the adhesive-coated side (the area symmetrically opposite about the fibrous sheet 1) as illustrated in FIG. 2(b). The alternative embodiment exhibits excellent effect in preventing strike-through similarly to the embodiment of FIG. 2(a). While in FIGS. 2(a) and 2(b) ink drops are schematically depicted for the sake of simplicity, they adhere to the surface not only of the adhesive layer but also of the fibers making up the fibrous sheet.

In the present embodiment, the printed breathable sheet 7 is dried in a dryer 8 immediately after the inkjet printing as illustrated in FIG. 1. Although the drying step is not always necessary, it accelerates ink drying to prevent smudging with undried ink more securely. Known drying systems including hot air drying and infrared drying can be used.

In the present embodiment, the breathable sheet 7 after drying step is laminated with another fibrous sheet 1', the same as the fibrous sheet 1, to give a breathable laminate sheet 7' composed of two fibrous sheets. In some detail, a fibrous sheet 1' unrolled from another roll is superposedly fed onto the hot melt adhesive coated side (the side with the adhesive layer 3) of the breathable sheet 7 from the dryer 8 being introduced into the nip of press rollers 9 and 10. The two sheets are bonded together via the adhesive layer 3 by pressing between the rollers 9 and 10 (the step of laminating). The step of laminating is optional. Understandably, the step of laminating is unnecessary in the production of a breathable sheet composed of a single fibrous sheet.

The process of producing an absorbent article according to the present invention will then be described with reference to its preferred embodiment by way of the accompanying drawings.

Figure 3:
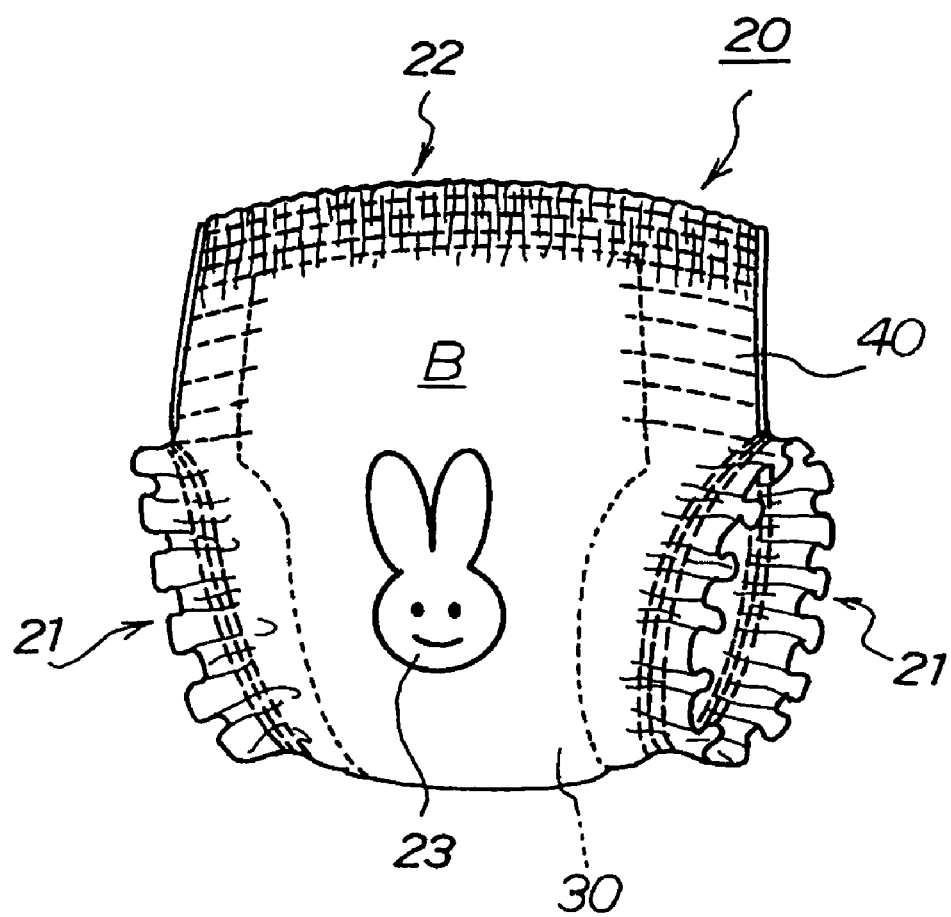
FIG. 3 is a perspective of an absorbent article (a pull-on diaper) according to the present invention, seen from its back side.
Figure 4:
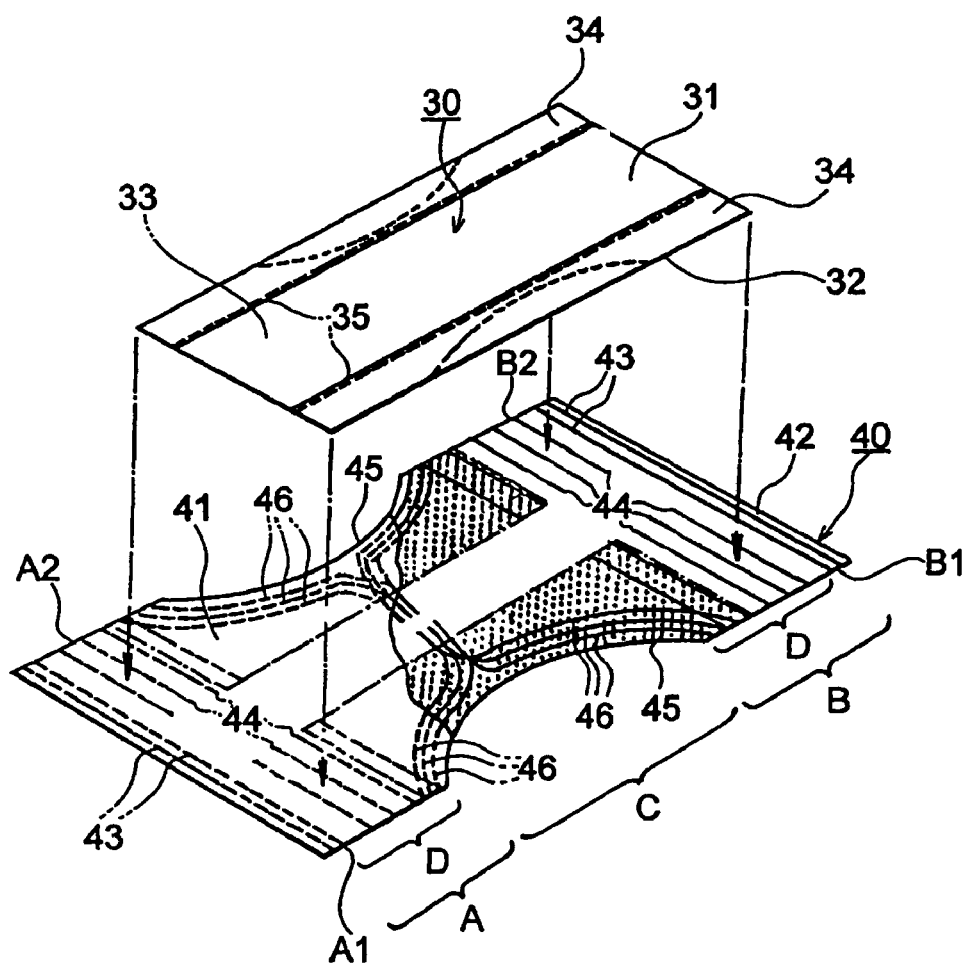
FIG. 4 is an exploded perspective view of the absorbent member shown in FIG. 3 in its unfolded, stretched out state.
Figure 6A:
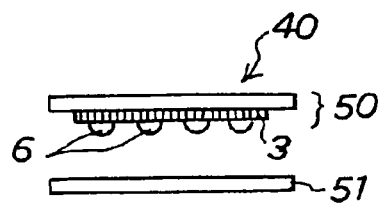
FIG. 6(a), FIG. 6(b), FIG. 6(c), and FIG. 6(d) each schematically illustrate the exploded structure of the exterior laminate used in the absorbent article shown in FIG. 3.
Figure 6B:
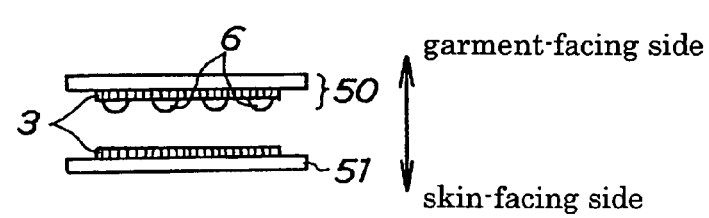
Figure 6C:
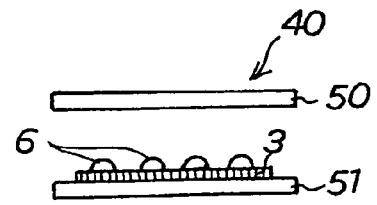
Figure 6D:
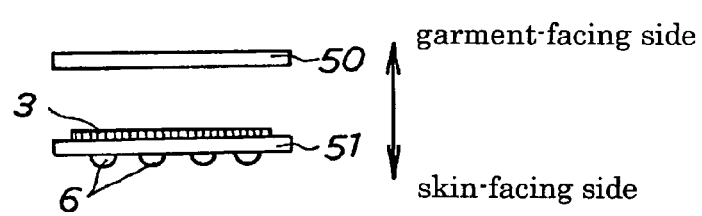

FIG. 3 is a perspective of a pull-on type disposable diaper as an embodiment of the absorbent article produced by the production process according to the present invention, seen from the backside of the diaper. FIG. 4 is an exploded perspective of the disposable diaper of FIG. 3 in its opened and stretched out state.

As illustrated in FIGS. 3 and 4, the diaper 20, an object of the production process according to the present embodiment, has an absorbent body 30 and an exterior laminate 40 disposed on the garment facing side (opposite to the skin facing side) of the absorbent body 30. The exterior laminate 40 is composed of two fibrous sheets 41 and 42. The exterior laminate 40 has a printed pattern 23 on a part of the fibrous sheets 41 and 42.

The diaper 20 is sectioned into a front portion A that is to be applied to the stomach side of a wearer, a rear portion B that is to be applied to the back side of a wearer, and a crotch portion C positioned between the front portion A and the rear portion B. Both lateral side edges A1 and A2 of the front portion A and both lateral side edges B1 and B2 of the rear portion B are joined together, respectively, by heat sealing, radiofrequency sealing, ultrasonic sealing, adhesive application or any other known bonding means to form a pair of leg openings 21 and a waist opening 22. The exterior laminate 40 (composed of the fibrous sheets 41 and 42) has a printed pattern 23 recognizable from the outside.

The absorbent body 30 has an oblong rectangular shape. It is adhesively disposed on the central portion of the exterior laminate 40 with its longitudinal direction coinciding with the longitudinal direction of the diaper 20. The term "longitudinal direction" (sometimes, "length direction") as used with respect to the diaper 20 is a direction connecting the front portion A and the rear portion B when the diaper 20 is opened flat.

The absorbent body 30 is composed of a liquid permeable topsheet 31, a liquid impermeable backsheet 32, and a liquid retentive absorbent core 33. The absorbent core 33 has its longitudinal middle part narrowed to make a sandglass shape and is fixedly held between the topsheet 31 and the backsheet 32. A pair of standing cuffs 34 are provided along the longitudinal side edges of the absorbent body 30. The standing cuff 34 has its base fixed along the longitudinal side edge of the absorbent body 30 with its free end directed to the widthwise middle of the absorbent body 30. The standing cuff 34 has a plurality of elastic members 35 (only one elastic member 35 is depicted in FIG. 4) disposed in its stretched out state so as to develop extensibility, whereby the standing cuff 34 stands up to block a body fluid from flowing laterally.

The exterior laminate 40 is composed of two fibrous sheets 41 and 42, which are nonwoven fabric. The exterior laminate 40 has its longitudinal middle portion narrowed in conformity to the contour of wearer's legs to make a sandglass shape.

Elastic members are disposed in specific sites between the two fibrous sheets 41 and 42 constituting the exterior laminate 40. Specifically, waist elastic members 43 are extensively arranged in a waist portion defining the waist opening 22 to form a waist gather substantially continuous over the whole waist circumference. Below-waist elastic members 44 are arranged in a below-waist portion D in each of the front portion A and the rear portion B along the diaper width direction at a predetermined interval in the diaper length direction. The below-waist portion D is a portion below the waist portion where the waist elastic members 43 are disposed and above the crotch portion C (the portion of the diaper with a narrowed width to form the pair of leg openings 21). Leg elastic members 46 are arranged in a pair of leg portions 45 defining leg openings 21 and across the crotch portion C to form a pair of leg gathers.

The process of producing the absorbent article (diaper 20) of the present embodiment is now described. To begin with, the exterior laminate 40 having a desired printed pattern and the absorbent body 30 are prepared.

The exterior laminate 40 having a printed pattern can be prepared by utilizing the above-mentioned process of producing a breathable sheet. An example of the production of the exterior laminate will be described with reference to FIGS. 5(a) through 5(c).

As illustrated in FIG. 5(a), a hot melt adhesive is applied to at least one of the two fibrous sheets (the sheet 41 in this particular embodiment) making the exterior laminate in a prescribed pattern to form a hot melt adhesive coated area H1 and a non-coated area H2 on one side of the sheet 41. A desired pattern 23 is inkjet printed on either (1) the coated area H1 or (2) the other side of the fibrous sheet 41 within an area corresponding to the coated area H1 (the area symmetrically opposite to the coated area H1 about the fibrous sheet 41).

As illustrated in FIG. 5(*b*), waist elastic members 43, below-waist elastic members 44, and leg elastic members 46 are spacedly introduced in their stretched state with the adhesive, and the fibrous sheets 41 and 42 are laminated on each other with the elastic members fixedly sandwiched therebetween (the step of laminating). The two fibrous sheets 41 and 42 must be superposed such that the pattern 23 printed on the fibrous sheet 41 may not be exposed outward. That is, the printed side of the fibrous sheet 41 should be covered with the fibrous sheet 42. If the printed pattern 23 is exposed outward, it can come off by abrasion.

The feeding position of the leg elastic member 46 is reciprocated in direction Y perpendicular to the machine direction of the fibrous sheet of continuous length (direction X). In the example displayed in FIG. 5(*b*), the two fibrous sheets 41 and 42 are joined together immediately after the elastic members 43, 44, and 46 are introduced. As a result of this step of introducing the elastic members and laminating the sheets, the sheets 41 and 42 are bonded over the coated area H1 to provide a bonded region P1. In the non-coated area H2, the two sheets 41 and 42 are not bonded to provide a non-bonded region P2. The waist elastic members 43, the below-waist elastic members 44, and the leg elastic members 46 are fixed between the sheets 41 and 42 in the bonded region P1 but not fixed in the non-bonded region P2.

In the step shown in FIG. 5(*c*), the below-waist elastic members 44 and the leg elastic members 46 are cut at a prescribed position (the step of cutting). Various known cutting tools can be used to carry out the step of cutting, including a pinch cutter, a rotary die cutter, a heat seal cutter, an ultrasonic cutter, and a water jet cutter. If desired, a prescribed part of the below-waist elastic members 44 and the leg elastic members 46 to be cut or having been cut may be fixed between the sheets 41 and 42 by heat sealing before, after, or simultaneously with the cutting step.

For the sake of simplicity, the pattern 23 is not depicted in FIGS. 5(*b*) and 5(*c*).

The step of introducing the elastic members such as rubber strands between the sheets 41 and 42 and laminating the two sheets as illustrated in FIGS. 5(*a*) to 5(*c*) is simpler than when the elastic members such as rubber strands are disposed in an independent step.

There is thus obtained a laminate sheet 40' of continuous length, which is then cut to length and trimmed to remove unnecessary parts 47 to give the exterior laminate 40.

In the present embodiment, the absorbent body 30, which is prepared separately in a usual manner, is bonded to the resulting exterior laminate 40 by a known bonding means. The side edges A1 and A2 of the front portion A and the side edges B1 and B2 of the rear portion B are joined together, respectively, to provide the pull-on disposable diaper 20.

The topsheet 31, the backsheet 32, and the absorbent core 33 that make up the absorbent body 30 and the elastic members used in the exterior laminate 40 can be of any materials commonly employed in disposable diapers of this type. The fibrous sheets of the exterior laminate 40 can be of synthetic paper or woven fabrics as well as nonwoven fabrics as previously stated.

The exterior laminate used in the present invention is a laminate of at least one breathable fibrous sheet with a printed pattern and at least one fibrous sheet with no printed pattern.

What is important in joining these sheets into an exterior laminate is that the printed pattern (ink layer) should not be exposed on the outer side of the absorbent article (diaper 20). As long as that requirement is satisfied, the order of superposing the sheets is not particularly limited. Particularly preferred structures of the exterior laminate 40 include three structures illustrated in FIGS. 6(*a*) through 6(*d*), each schematically representing an exploded cross-sectional view of the exterior laminate 40 composed of at least two fibrous sheets 50 and 51.

In the first structure shown in FIGS. 6(*a*) and 6(*b*), the outermost sheet 50 (the sheet farthest from a wearer's body) is the sheet having the adhesive layer 3 (coated area) formed on its skin facing side and an ink 6 adhered (a pattern printed) on the skin facing side of the adhesive layer 3. The difference between FIGS. 6(*a*) and 6(*b*) resides in that the inner sheet 51, which is bonded to the skin facing side of the outermost layer 50, has an adhesive layer 3 on its garment facing side in FIG. 6(*b*). The first structure inclusive of the one shown in FIG. 6(*a*) and the one shown in FIG. 6(*b*) are advantageous in that strike-through of inkjet ink does not occur so that the ink pattern is clearly recognizable form the outside and is safe to the wearer's skin and that the ink (colorant), adhering directly to the adhesive layer, exhibits excellent color fastness. Since the part of the adhesive layer 3 to which the ink 6 adheres is not bonded to the inner sheet 51, the printed pattern is raised partly to look three-dimensional. The structure of FIG. 6(*a*) is particularly excellent in sheet flexibility because of the relatively small thickness of the adhesive layer, and that of FIG. 6(*b*) is particularly excellent in pattern retention because of the doubled adhesive layer.

In the second structure shown in FIG. 6(*c*), the inner sheet 51 adjacent to the outermost sheet 50 is the sheet having the adhesive layer 3 on its garment facing side and the ink 6 adhered on the garment facing side of the adhesive layer 3. The second structure produces excellent effects similarly to the first structure.

In the third structure shown in FIG. 6(*d*), the inner sheet 51 adjacent to the outermost sheet 50 is the layer having the adhesive layer 3 on its garment facing side and the ink 6 adhered on its skin facing side in the area corresponding to the adhesive layer 3 on the garment facing side. Similarly to the first and the second structures, the third structure is excellent in preventing ink from striking through and the printed ink from coming off, and the ink hardly comes into contact with the skin.

While the present invention has been described with particular reference to the embodiments thereof, it should be understood that the invention is not construed as being limited thereto, and various changes and modifications can be made therein without departing from the spirit and scope thereof as exemplified as follows.

After inkjet printing, the printed ink (pattern) may be overcoated with a relatively small amount of a hot melt adhesive. This modification is particularly preferably applied to the structure of FIG. 6(*c*). By overcoating the ink 6 with a hot melt adhesive, the ink 6 is fixed more securely, and the two fibrous sheets 50 and 51 are bonded with increased adhesion.

Applying a hot melt adhesive only to the vicinity of the printed pattern discretely in the machine direction is preferred to provide a flexible exterior laminate.

While in the foregoing embodiment of the production of the absorbent member (disposable diaper 20) the two sheets composing the exterior laminate are fibrous sheets of a kind, the sheet that is not printed may be replaced with, for example, a non-perforated film or a sheet with fine pores. In that modification, both the upper and the lower sides of the absorbent core 33 may be covered with the liquid permeable topsheet 31 without using the backsheet 32.

While in the above embodiment the exterior laminate of the diaper 20 is composed of two fibrous sheets, the exterior laminate may be composed of a single fibrous sheet, in which case the fibrous sheet having a pattern printed is directly bonded to the absorbent body 30.

The production process of an absorbent article according to the present invention is applicable to flat type disposable diapers having a pair of fastening tapes as well as the above-described pull-on disposable diapers. The process is also applicable to the production of sanitary napkins and non-woven fabrics for commercial packages.

In the production process of a breathable sheet according to the present invention, a hot melt adhesive is applied to a fibrous sheet such as nonwoven fabric, and inkjet printing is carried out on the adhesive coated area of the adhesive coated side of the fibrous sheet or the opposite side of the fibrous sheet in an area corresponding to the adhesive coated area. According to the process, ink drops ejected from an inkjet head are caught on the hot melt adhesive so that ink strike-through is effectively prevented. Various troubles arising from ink strike-through, such as soiling the production line or the product with ink, reduction in printing speed, and reduction in printed image density, can be avoided. The hot melt adhesive ensures ink fixability to provide a printed breathable sheet with improved colorfastness and resistance to pattern coming off.

In the production process of an absorbent article according to the present invention, a member having a pattern printed (an exterior laminate) is prepared by the production process of a breathable sheet. Therefore, the resulting absorbent article has a printed pattern with excellent visibility and color fastness. It is desired for the exterior laminate of an absorbent article not to have an ink layer applied to its part of an outer surface or an inner surface, that possibly comes into contact with the skin. From this viewpoint, the absorbent article produced by the process of the present invention has no fear of ink's adhering to the skin contact surface thereof because ink strike-through is effectively prevented as stated above.

What is claimed is:

1. A process of producing an absorbent article having an absorbent body and an exterior laminate on the garment facing side of the absorbent body, the exterior laminate comprising a fibrous sheet having a pattern printed, the process comprising the steps of:
    applying a hot melt adhesive to one side of the fibrous sheet,
    inkjet printing the pattern on the side of the fibrous sheet in the area having the hot melt adhesive applied or on the other side of the fibrous sheet in the area corresponding to the area having the hot melt adhesive applied to prepare a printed fibrous sheet at a printing speed of 100 m/min or higher wherein the step of inkjet printing is carried out while the hot melt adhesive applied to the fibrous sheet is at a temperature of 40° C. or higher; and
    disposing the printed fibrous sheet as a member of the exterior laminate on the absorbent body with the printed side thereof not being exposed outward,
    wherein the exterior laminate comprises the printed fibrous sheet and a non-printed fibrous sheet;
    wherein the area having the applied hot melt adhesive comprises a continuous hot melt adhesive film having fine through-holes; and
    wherein the step of laminating the printed fibrous sheet and a non-printed fibrous sheet is carried out after the inkjet printing.

2. A process of producing a breathable sheet having a pattern printed thereon, comprising the steps of:
    applying a hot melt adhesive to one side of a fibrous sheet containing natural fiber as a major component or a nonwoven fabric and
    inkjet printing the pattern on the other side of the fibrous sheet in the area corresponding to the area having the hot melt adhesive applied at a printing speed of 100 m/min or higher;
    wherein the step of inkjet printing is carried out while the hot melt adhesive applied to the fibrous sheet is at a temperature of 40° C. or higher; and
    wherein the area having the applied hot melt adhesive comprises a continuous hot melt adhesive film having fine through-holes.

3. A process of producing a breathable sheet having a pattern printed thereon, comprising the steps of:
    applying a hot melt adhesive to one side of a fibrous sheet containing natural fiber as a major component or a nonwoven fabric and
    inkjet printing the pattern on the side of the fibrous sheet in the area having the hot melt adhesive applied or on the other side of the fibrous sheet in the area corresponding to the area having the hot melt adhesive applied at a printing speed of 100 m/min or higher;
    wherein the step of inkjet printing is carried out immediately after hot melt adhesive application and while the hot melt adhesive applied to the fibrous sheet is at a temperature of 40° C. or higher; and
    wherein the area having the applied hot melt adhesive comprises a continuous hot melt adhesive film having fine through-holes.

* * * * *